United States Patent [19]
Mage et al.

[11] Patent Number: 5,026,785
[45] Date of Patent: Jun. 25, 1991

[54] AVIDIN AND STREPTAVIDIN MODIFIED WATER-SOLUBLE POLYMERS SUCH AS POLYACRYLAMIDE, AND THE USE THEREOF IN THE CONSTRUCTION OF SOLUBLE MULTIVALENT MACROMOLECULAR CONJUGATES

[75] Inventors: Michael Mage, Bethesda; Bernardetta Nardelli, Kensington; Louise McHugh, Bethesda, all of Md.

[73] Assignee: The United States of America as represented by the Department of Health and Human Services, Washington, D.C.

[21] Appl. No.: 351,042

[22] Filed: May 12, 1989

[51] Int. Cl.$^5$ .................. C08F 120/56; C08F 8/12; C08F 8/30; C01N 33/546
[52] U.S. Cl. .................. 525/329.4; 525/374; 525/377; 424/78; 424/81; 436/532; 436/533; 436/534
[58] Field of Search ............ 525/329.4, 374, 377; 424/78, 81; 436/532, 533, 534

[56] References Cited
U.S. PATENT DOCUMENTS
4,582,810 4/1986 Rosenstein .................. 436/181

Primary Examiner—Joseph L. Schofer
Assistant Examiner—Thomas McDonald, Jr.
Attorney, Agent, or Firm—Birch, Stewart, Kolasch and Birch

[57] ABSTRACT

Avidin and streptavidin modified water-soluble polymers are provided, such modified polymers being exemplified by, but not limited to, water-soluble polyacrylamides being substituted by multiple substituents of avidin or streptavidin. The avidin and streptavidin modified polymers provided, may be stored, and later used to bind biotinylated antibiodies, biotinylated toxins, or biotinylated isotope-labelled proteins, thus producing homo- or heteroconjugates of known composition. A process for the preparation of certain of the avidin or streptavidin modified polymers and conjugates thereof is also provided.

6 Claims, 3 Drawing Sheets

AVIDIN AND STREPTAVIDIN MODIFIED WATER-SOLUBLE POLYMERS SUCH AS POLYACRYLAMIDE, AND THE USE THEREOF IN THE CONSTRUCTION OF SOLUBLE MULTIVALENT MACROMOLECULAR CONJUGATES

BACKGROUND OF THE INVENTION

In recent years natural and artificial soluble polymers have been bound to haptens (Inman 1975, Siciliano et al, 1985) or to proteins (Abramenko et al, 1983) or prepared as copolymers with oligosaccharides (Kochetkov et al, 1982), to create interesting T-independent antigens and T cell stimulating molecules (Inman, 1975; Siciliano et al, 1985; McKluskey et al, 1988) immunotoxins (Printseva et al, 1985) and immunodrugs (Rihova et al, 1986). Proteins non-covalently linked to artificial polycations have also been reported to behave as T-independent antigens (Vinogradov, 1982). Carbodiimide (CDI) has been used to link proteins to each other, or to polymers (Petrov et al, 1979; Abramenko et al, 1983).

SUMMARY OF THE INVENTION

Attempts to develop reagents for specifically coating tumor cells with antigens that might sensitize them to immune cytolysis has led us to the use of water-soluble polymer-protein conjugates, and more specifically, to the use of substantially linear polyacrylamide-based polymer-protein conjugates (polygens). By coupling substantially linear polyacrylamide (PA) with streptavidin (SA) or avidin (A), the convenient general reagents avidin modified polyacrylamide, of which polyacrylamide-avidin (PAA) is a type; and streptavidin modified polyacrylamide, of which polyacrylamide-streptavidin (PASA) is a type have been provided herein. Any of the above avidin or streptavidin modified polymers, provided herein, may be used to prepare multivalent macromolecular conjugates, by coupling any of the same with a wide variety of biotinylated proteins. The preparation of such macromolecular conjugates is based upon a known interaction between biotin and avidin (Bayer and Wilchek, 1980).

With the utilization of PASA or PAA, provided herein, we have prepared water-soluble multivalent heteroligating antibody conjugates capable of binding cells of different MHC haplotypes, as well as heteroconjugates of anti-Class I MHC antibodies and soluble Class I MHC molecules; these conjugates have been used to coat murine tumor cells with allogeneic Class I MHC molecules. The same procedure has the potential for, and is fully envisioned as, being useful in the preparation of a wide range of "off the shelf" ad hoc multivalent conjugates. Such multivalent conjugates could be either immunotoxins, tumor labeling reagents, or vaccines easily prepared by mixing any of a variety of biotinylated antibodies or toxins or isotope-labelled proteins or unlabelled proteins or peptides with any of the avidin or streptavidin modified water-soluble polymers disclosed herein, including avidin modified polyacrylamide, streptavidin modified polyacrylamide, polyacrylamide-streptavidin (PASA) and polyacrylamide-avidin (PAA).

The present invention is also directed to a simplified procedure for making biotinylated protein conjugates with certain avidin and streptavidin modified polymers, disclosed herein, more specifically, avidin modified polyacrylamide, streptavidin modified polyacrylamide, PASA and PAA.

Several features of applicants, process for preparing avidin and streptavidin modified polyacrylamides, including PASA and PAA should be noted. First, in contrast to previous uses of a carbodiimide to link proteins to each other or to polymers, in an aqueous environment, in the present invention activated polyacrylamide is separated from excess carbodiimide prior to adding avidin or streptavidin. This removal of excess carbodiimide prevents intermolecular crosslinking of avidin or streptavidin protein by a carbodiimide. Secondly, in contrast to prior processes, applicants, during the coupling step of avidin or streptavidin to polyacrylamide, utilize excess avidin or streptavidin to inhibit intermolecular crosslinking of polyacrylamide. Thirdly, in contrast to prior processes, by utilizing applicants' processes, once the capacity of avidin modified polyacrylamide, streptavidin modified polyacrylamide, PASA or PAA for biotinylated proteins has been measured, and appropriate biotinylated proteins prepared, preparation of conjugates requires no further activation, use of crosslinking agents, or purification from unbound protein and crosslinking agent.

Applicants' furthermore note that their processes, provided herein, have utility for preparing a variety of multivalent water-soluble macromolecular heteroconjugates of known composition for uses such as immunotoxins, tumor labeling reagents, complex antigens, and in multivalent arrays of cell interaction molecules for studying low affinity interactions such as those postulated to occur between the T cell receptor and shelf MHC molecules.

Accordingly, the present invention provides for the following:

1) An avidin or streptavidin modified water-soluble polymer, comprising:
   a water-soluble polymer, substituted by multiple avidin or streptavidin substituents.

2) An avidin or streptavidin modified water-soluble polyacrylamide, comprising:
   a water-soluble, polyacrylamide substituted by multiple substituents of avidin or streptavidin.

3) An avidin or streptavidin modified polyacrylamide, comprising:
   a substantially linear, water-soluble polyacrylamide having an average molecular weight of 20,000 to $2 \times 10^6$ daltons substituted by multiple molecular substituents of avidin or streptavidin.

4) An avidin or streptavidin modified polyacrylamide, comprising:
   a substantially linear, water-soluble polyacrylamide having an average molecular weight of about $1 \times 10^6$ daltons substituted by about 10-50 substituents of avidin or streptavidin.

5) An avidin or streptavidin modified polyacrylamide, prepared by the process steps of:
   (I) converting about 1 to 50% of the amide groups of a substantially linear, polyacrylamide into carboxyl groups;
   (II) activating, in an aqueous solution, subsequent to step (I), certain carboxyl groups on said polyacrylamide, with an excess of a carbodiimide;
   (III) separating the resultant product of step (II) from said excess of said carbodiimide;
   (IV) reacting, subsequent to Step (III), said resultant product with an excess of avidin or streptavidin, and thereby forming said avidin or streptavidin modified polyacrylamide in situ; and (V) separating, subsequent to step (IV), said avidin or streptavidin modified polyacrylamide from excess streptavidin or avidin.

6) Any of the above avidin or streptavidin modified polymers provided herein, in (1) to (5), additionally substituted by a variety of either biotinylated antibodies, or biotinylated toxins, or soluble biotinylated isotope-labeled proteins.

7) A process for the preparation of an avidin or streptavidin modified polyacrylamide, comprising the process steps of:

(I) converting about to 50% of the amide groups of a substantially linear, polyacrylamide into carboxyl groups;

(II) activating, subsequent to step (I), certain carboxyl groups on said polyacrylamide with an excess of a carbodiimide;

(III) separating the resultant product of step (II) from said excess of said carbodiimide;

(IV) reacting, subsequent to step (III), said resultant product with an excess of avidin or streptavidin, and thereby forming said avidin or streptavidin modified polyacrylamide in situ: and (V) separating, subsequent to step (IV), said avidin or streptavidin modified polyacrylamide from excess streptavidin or avidin.

In order to remove any ambiguity which may exist as to what certain terms utilized herein should be understood to encompass, the following glossary is provided.

The term "water-soluble polymer" as used herein means polymers which are biologically acceptable and compatible in a human, and which are completely soluble in two parts of purified water, USP, at about 23° C. on a weight/weight basis, exemplary of such are certain polyacrylamides, dextrans, polyglutamic acids, polyacrylic acids, polyethylene glycol and the like.

The term "polyacrylamide" as used herein means an acrylamide polymer comprising repeating units having the structure

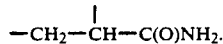

The term "substantially linear polyacrylamide" means a polyacrylamide as defined above having minimal or zero crosslinking, preferably zero crosslinking.

The term "carbodiimide" as used herein means cyanamide and its associated derivatives. More specifically, we include 1-ethyl-3(3-dimethylaminopropyl)carbodiimide within the definition utilized herein.

The term "avidin" as used herein means a factor isolatable from raw egg whites, capable of producing biotin deficiency in rats and chicks. Its structure is a glycoprotein containing essentially four identical subunits. The combined molecular weights of the subunits is about 66,000 daltons. For a general review of avidin, see Green, Av. Protein Chem., Vol. 29, pp. 85-133 (1975).

The term "streptavidin" as used herein means avidin produced by the streptomyces microorganism as described by Pahler et al, J. Biol. Chem. 262:13933 (1987).

The term "biotinylated antibody" as used herein means an antibody molcule covalently substituted with one or more biotin molecules, by means such as are described by Bayer and Wilchek, Meth. Biochem. Anal. 26:1, 1980.

The term "biotinylated toxins" as used herein means a protein toxin molecule, or a toxic fragment of such a molecule covalently substituted with one or more biotin molecules, by means such as are described by Bayer and Wilchek, Meth. Biochem. Anal. 26:1, 1980.

The term "biotinylated isotope-labelled proteins" as used herein means molecules of isotope-labelled proteins, covalently substituted with one or more biotin molecules per protein molecule, by means such as are described by Bayer and Wilchek, Meth. Biochem. Anal. 26:1, 1980.

The term "variety of biotinylated antibodies, or biotinylated toxins or biotinylated isotope-labelled proteins means a mixture of at least 2 or more different biotinylated antibodies, or at least 2 or more different biotinylated toxins, or at least 2 or more different biotinylated isotope-labelled proteins.

The term "molecular weight" as utilized herein when referring to a polymer's molecular weight, means the molecular weight of a polymer as determined by size exclusion chromatography. Exemplary of a suitable column on which to perform size exclusion chromatography, to determine a polymer's molecular weight, is a Bio-Rad "Bio-gel DNA XL Column" or the like.

DETAILED DESCRIPTION OF THE INVENTION

Figure 1:
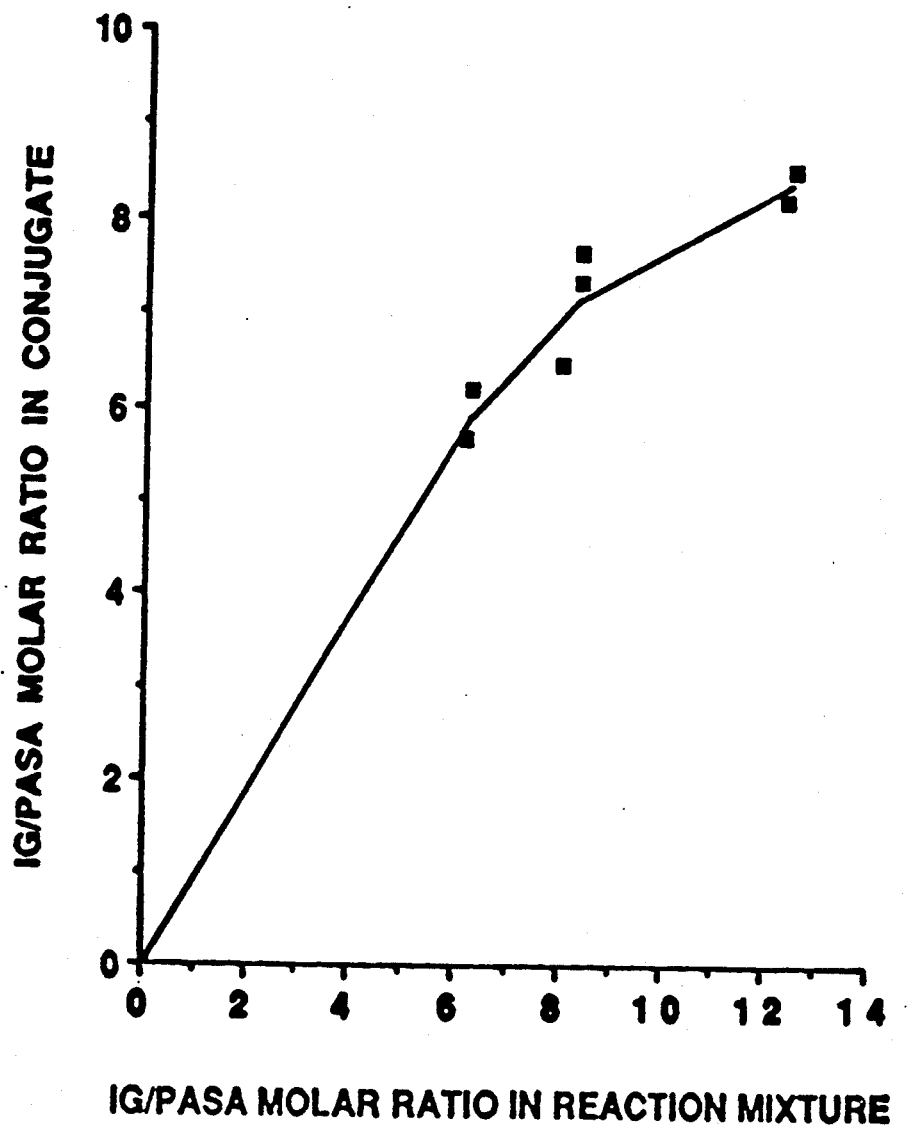
FIG. 1. Binding capacity of polyacrylamide-streptavidin (PASA) for biotinylated antibody molecules, calculated from the absorbance of excluded and included peaks from size exclusion chromatography of mixtures of PASA and immunoglobulin.

The following description is meant to aid those skilled in the art in practicing the present invention, and while the discussions, provided herein, are sometimes limited to instances wherein a polyacrylamide has been chosen as the water-soluble polymer, such instances should not be construed to limit any other disclosed aspects of present invention, including the use of a variety of water-soluble polymers.

This is particularly true, because certain water-soluble polymers, provided herein as useful in the present invention, may be substituted with multiple substituents of avidin or streptavidin, without the generation of carboyxl groups thereon (e.g., polyacrylic acids and polyglutamic acids) and moreover because carboxyl groups naturally occurring on the same, may be activated with polymer "cross-linkers" other than carbodiimides. Applicants, realizing the same, only limit the use of water-soluble polymers to those being biologically acceptable and compatible in humans, and capable of being substituted by multiple substituents of avidin or streptavidin, without unduly difficult and lengthy processes when compared to processes disclosed herein.

The detailed description concludes with an Experimental Section.

The present invention provides for products, wherein water-soluble polymers such as water-soluble polyacrylamide have been substituted by either multiple avidin or streptavidin substituents. Methods for preparing such products wherein polyacrylamides are the water-soluble polymers are also provided. Inasmuch as the process for preparing polyacrylamide based products, provided herein, utilizes as raw materials water-soluble polyacrylamides, as well as other starting materials, a discussion of suitable starting materials useful in such a process will be incorporated into the following discussion of process steps utilized to prepare avidin modified polyacrylamides, of which PAA is an example, and, streptavidin modified polyacrylamides, of which PASA is an example.

Step I - Converting Amide Groups

In order to prepare any of the modified polyacrylamide products provided herein, including PASA and PAA, by processes provided herein, one necessarily starts with a polyacrylamide. An acceptable starting polyacrylamide must be water-soluble, and is preferably also substantially linear, i.e., having preferably minimal to zero crosslinking of the repeating units which comprise the polymer, although the same is not mandatory. Furthermore, with respect to preferred starting polyacrylamide raw materials, we note that the term substantially linear does not foreclose the use of substantially linear polyacrylamides having branching thereon, and therefore, branched polyacrylamide can also be preferred starting materials herein. Since such a branched polyacrylamide's backbone is, of course, still substantially linear.

Additionally, it is thought that suitable starting polyacrylamides should have an average molecular weight of between about 50,000 daltons to $2 \times 10^6$ daltons. Within this range of acceptable average molecular weights, it is thought that one would preferably choose a polyacrylamide with an average weight of about $1 \times 10^6$ daltons, but the same is not mandatory, and any polyacrylamide having an average molecular weight falling within the above cited range is acceptable.

Finally, again we note that a suitable starting polyacrylamide raw material must be soluble in an aqueous based solution inasmuch as avidin and streptavidin modified polyacrylamide products produced therefrom, including PASA and PAA, are to be soluble in aqueous based solutions. All polyacrylamides encompassed herein being within the average molecular weight range provided (i.e., between about 50,000 to $2 \times 10^6$ daltons), and if substantially linear, should readily meet with this requirement. If, however, one finds a polyacrylamide which might otherwise would be a suitable starting polyacrylamide raw material, but which is not completely soluble in 2 parts purified water, USP, on a weight per weight basis at a temperature of about 23° C., the same is expressly excluded herefrom.

In performing a conversion of approximately 1-50% of amide groups (—C(O)NH$_2$) into carboxyl groups (—C(O)OH) on a chosen polyacrylamide, it is thought that an appropriate and preferred method for performing the conversion is by the use of alkaline hydrolysis at a pH of about 9-11, and thereafter removing ammonia created in situ. It is also envisioned, however, that one can utilize acid hydrolysis of a chosen polyacrylamide at acidic pH's to convert 1-50% of amide groups into carboxyl groups, and the same is considered encompassed by methods herein provided, unless expressly excluded.

Step II - Activating Amide Groups

Once a desired number of amide groups (1-50%) have been converted to carboxyl groups on the originally chosen polyacrylamide, certain of these created carboxyl groups are activated. The activation of these carboxyl groups is achieved by reaction with, in the presence of an aqueous based solution, an excess of a carbodiimide. If so desired, one may alternatively activate carboxyl groups with polymer cross-linkers other than carbodiimides (see, e.g., Pierce Chem. Co. catalog for a list of suitable crosslinking agents). Generally, we have activated carboxyl groups herein with the carbodiimide 1-ethyl-3-(3-dimethylaminopropyl)carbodiimide, but the same is not mandatory, and the use of compounds such as dicyclohexylcarbodiimide (i.e., $C_6H_{11}$—N=C=N—$C_6H_{11}$), or, other derivatives of cyanamide (i.e., $H_2NC\equiv N$) are also considered encompassed hereinunless the same are expressly excluded.

It is noted that while carbodiimides are cross-linker compounds, as used herein their principle function is to activate carboxyl groups for the attachment of avidin or streptavidin to a water-soluble polymer, and not to cross-link a water-soluble polymer's molecular strands to each other.

When activating carboxyl groups on a chosen polyacrylamide, it is thought that a suitable temperature is about 0° C., and a suitable pH is about 2-3. When activating with 1-ethyl-3-3-dimethylaminopropyl)carbodiimide, or another carbodiimide, it is thought that under the above conditions, activation can be achieved in a matter of about 10-15 min, but the same should not be considered limiting. We note that the use of higher temperatures and pH's may additionally be utilized when activating carboxyl groups with a carbodiimide, but that activation at these higher pH's, up to about pH 5, and temperatures, up to about 23° C., are not preferred, inasmuch as higher pH's and temperatures are thought to adversely affect the half-lives of activated carboxyl groups produced. In any event, the use of a carbodiimide to activate certain carboxyl groups on carboxylated polyacrylamide should proceed as shown in the following reaction scheme Ia:

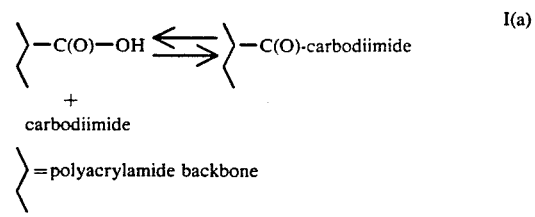

I(a)

Lastly, it is again noted that while in our discussion of Step II herein, we activate carboxyl groups with a carbodiimide, it should be realized that almost any of a variety of compounds known in the art to "crosslink" polymers could be used in the place of a carbodiimide. As such the use of such known "crosslinkers" in the present process (i.e., to primarily activate carboxyl groups and not crosslink polymeric molecular strains to each other) is considered an obvious varient of the method taught herein, and considered encompassed herein.

Step III - Separating Out Resultant Product

We note, that once certain carboxyl groups of a carboxylated polyacrylamide have been activated, the activated carboxyl groups have a half-life of about 1 hr at a temperature of 0° C. Therefore, it is felt preferable to maintain the activated polyacrylamide at about this temperature or a lower temperature while excess carbodiimide is removed from the reaction mixture. In performing the separation of excess carbodiimide, it was found that chromatographing on a G25 Sephadex column at 0° C. produced satisfactory separation results.

While the above type separation was used herein, it is also envisioned that column chromatography on different types of columns should be immediately apparent to those skilled in the art, and the same is considered encompassed herein. Moreover, other non-chromatographic separation techniques readily known by those in the art are also considered encompassed within the present invention, it only being necessary that such techniques produce a satisfactory separation of an excess of a carbodiimide from the desired activated polyacrylamide, and that such technique not be unduly lengthy, so as to allow too many activated carboxyl groups to become unactivated, due to their short half-lives.

Step IV - Reacting With Avidin or Streptavidin

Once the excess of carbodiimide has been removed from the desired activated polyacrylamide, the activated polyacrylamide should immediately thereafter be reacted with an excess of either avidin or streptavidin. A suitable reaction temperature is thought to be about 0° C., and a suitable pH is thought to be about 8-9. However, it is also realized that temperatures of up to about 23° C. may be utilized, in coupling avidin or streptavidin to an activated carboxyl group, and the same is considered encompassed by the methods herein provided unless expressly excluded.

When avidin or streptavidin couples to activated polyacrylamide, it occurs by the reaction scheme of I(b):

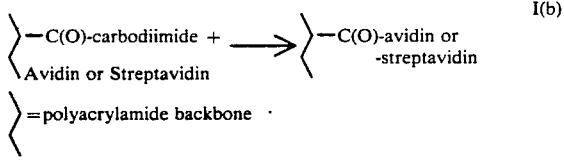

As should be apparent from reaction scheme I(b), in order to couple avidin or streptavidin to polyacrylamide by methods provided herein it is necessary that activated carboxyl groups exist on a polyacrylamide backbone. Furthermore, we note that given reaction I(a), above, is reversable, there can exist carboxyl groups (i.e., C(O)OH) on the avidin or streptavidin modified polyacrylamides provided herein. The amount of such carboxyl groups on the avidin or streptavidin modified polyacrylamide ultimately produced, will depend upon the initial quantity of amide groups which are hydrolyzed into carboxy groups (i.e., 1-50%) and of these carboxy groups--how many are ultimately substituted by avidin or streptavidin, through the coupling process provided herein.

We note also that techniques are available to those skilled in the art to convert carboxyl groups, contained on a streptavidin or avidin modified polyacrylamide as provided herein, into amide groups. The use of such techniques should be readily apparent to those skilled in the art. For example, sulfonyl chloride may be utilized to convert carboxyl groups into acid chlorides, which are then reacted with ammonia to form amides. Use of such a technique is considered fully encompassed herein, and moreover, resulting avidin or streptavidin modified polyacrylamides produced utilizing such techniques are considered fully encompassed herein. Furthermore, due to the availability of such techniques, avidin and streptavidin modified polyacrylamide products not containing carboxyl groups are considered encompassed herein.

Step V - Separating Out Desired End Product

Once an avidin or streptavidin modified polyacrylamide has been produced in situ, it is separated from the reaction mixture. Such separations, as performed herein, utilized size exclusion chromatography, and the same is illustrated in the Experimental section contained herein. The use of such a chromatographic method is not considered limiting to the present invention, however, since other means of separation readily apparent to those skilled in the art could be utilized, without departing from the spirit and scope of the present invention. The only requirement for an appropriate separation technique is that it not be too unduly difficult, or produce unsatisfactory results.

Once step V has been completed, the resultant avidin or streptavidin modified polyacrylamide can be stored and later utilized as a chemical reagent to prepare any of a variety of multivalent protein-protein conjugates. For example, streptavidin modified polyacrylamides, provided herein, have been stored for up to four (4) months at about 0° C., and shown to remain stable. The use of any of the avidin or streptavidin polyacrylamides, provided herein, to form multivalent protein-protein conjugates after storing is considered encompassed herein. Moreover, we consider this to be one of the preferred embodiments of the present invention, inasmuch as such a method allows for the "ad hoc" or "off the shelf" preparation of an endless variety of multivalent protein-protein conjugates.

The above "ad hoc" or "off the shelf" method of preparation for an endless variety of multivalent protein-protein conjugates, would of course also be applicable to those avidin or streptavidin modified water-soluble polymers other than avidin and streptavidin modified polyacrylamides which are provided herein.

It is expected that utilization of the above "ad hoc" technique will allow those skilled in the art to efficiently and easily prepare multivalent conjugates with a variety of either biotinylated antibodies, biotinylated toxins, or biotinylated isotope labelled or unlabelled proteins. Moreover, such varieties of biotinylated antibodies, toxins, or isotope-labelled or unlabelled proteins, can be coupled to the avidin or streptavidin modified water-soluble polymers, provided herein, in conceivably any proportions or ratios desired.

In order to couple, for example, different ratios of different biotinylated antibodies to one of the avidin modified polyacrylamides provided herein, one only need add an appropriate amount of one of the avidin modified polyacrylamides, provided herein, to a suitable mixture of different biotinylated antibodies in ratios ultimately desirable for attachment to the avidin modified polyacrylamide mixed therewith. For example, if one introduces an avidin modified polyacrylamide into a suitable mixture contain twice as many molecules of a biotinylated antibody A, as there are of a biotinylated antibody B, then one would consider it expectable that a multivalent protein-protein conjugate would be formed between the avidin modified polyacrylamide and the biotinylated antibodies, wherein the resulting conjugate would be coupled to twice as many biotinylated A antibodies, as biotinylated B antibodies.

Inasmuch as the above coupling technique for preparing multivalent protein-protein conjugates is based upon the known interaction of biotin with avidin or streptavidin, the above example is not considered limiting to the present invention, and obvious varients thereof utilizing a biotin-avidin, or biotin-streptavidin coupling are considered encompassed herein.

The following Experimental Section is meant to further assist those skilled in the art in practicing the present invention. It should not be construed to limit the present invention, inasmuch as the present invention is only to be limited by the scope of the appended claims.

EXPERIMENTAL SECTION

Materials and Methods

Soluble, substantially linear, polyacrylamide (PA) with an average molecular weight of about one million Da was obtained as a dry powder from Polysciences. A standard solution was prepared by dissolving it to a concentration of 25 mg/ml in potassium phosphate buffer, pH 6.85 (0.125 M phosphate). Such a potassium phosphate buffer was also used for all the size exclusion chromatography mentioned subsequently. In order to measure PA concentration in subsequent procedures, an aliquot of the standard solution was passed through TSK size-exclusion columns (Bio-Rad) monitored with a Waters R403 differential refractometer. The area of the excluded peak is directly proportional to the PA concentration. This ratio of peak area per mg/ml of PA was used to calculate PA concentration in all subsequent procedures. Aliquots of the PA solution were hydrolyzed at pH 10 and dialyzed to remove ammonia. About 11% of the amide residues were converted to carboxyl groups, as measured by acid-base titration (Inman, 1974).

The murine tumor cell lines P815, EL4, and RDM4 have been maintained in NIH labs for year in RPMI 1640 medium with 10% fetal calf serum. It is noted that the same typing medium was used to maintain all other cell lines mentioned herein, and further that each of the above cell lines are on deposit with the American Type Culture Collection. The cell line producing monoclonal anti-H-2 Kk antibody 11.4.1 (Oi et al, 1978), was also obtained from the American Type Culture Collection. Anti H-2Dd antibody 34.2.12 and rat anti-mouse class I MHC hybridoma K204 were respectively provided by Drs. David Sachs and Ken Yamada, both of whom are researchers with the National Institutes of Health. However, it is also noted that both of these cell lines are also available from American Type Culture Collection, and are on deposit with the same. When tested by us, rat anti-mouse Class I hybridoma K204 reacted with most mouse cells, except those bearing the H-2 k haplotype. Antibodies were affinity purified from culture supernatants or ascites on columns of goat anti-mouse IgG bound to Sepharose 4B. Soluble Class I MHC antigens were prepared from liver membrane proteins (Henriksen et al, 1979) by: detergent solubilization; affinity chromatography on columns of monoclonal anti-class I MHC antibodies; and removal of the transmembrane and cytoplasmic domains by limited proteolysis, essentially by the procedure of Mescher et al, 1983, except that chymotrypsin was used for Dd antigen. Biotinylation of proteins was done with the biotin-N-hydroxysuccinimide by the method of Bayer and Wilchek, Meth. Biochem. Anal. 26:1, 1980. "Core" streptavidin, 47KDa (Pahler et al, 1987), was from Jackson Immunoresearch.

PA concentration was monitored in column effluents with a Waters R403 differential refractometer. Protein concentration was measured by absorbance at 280 nm, and/or by BCA assay (Smith et al, 1985). Biotin binding capacity was measured by mixing an aliquot of purified conjugate with tritiated biotin diluted with cold carrier, and separating bound from unbound biotin on a TSK250 size exclusion column (Bio-Rad).

Flow cytometry was done on a FACS Analyzer, configured essentially as described by Luce et al, 1985, with the manufacturers recommended filter packs for fluorescein versus phycoerythrin fluorescence. FITC-labeled mouse anti-rat kappa chain (B-D), and FITC-labeled F(ab')2 rat anti-mouse-IgG (Jackson Immunoresearch) were used to distinguish rat and mouse antibodies. In the heteroligating experiments, two million RDM4 cells (H-2k) were internally labeled with 200 μl of a 28 μg/ml solution of hydroethidine (HDE) (Luce et al, 1985) in fluorescence buffer (PBS containing 1 percent newborn calf serum and 0.01% NaN$_3$), for 40 minutes at room temperature. P815 cells (H-2d) were labeled in the same fashion with a 0.5 μg/ml solution of carboxyfluorescein diacetate (CFDA), (Calbiochem) for three minutes. Longer incubation with CFDA made the cells too bright for electronic compensation of CFDA emission crossover into the F2 photomultiplier. Subcellular size particles and unstained cells were gated out before calculating percent of heteroligated cells.

Results and Discussion

1. Activation of carboxylated polyacrylamide by a carbodiimide.

For activation, 6.0 mg of carboxylated polyacrylamide in 2.0 ml of phosphate buffer saline was adjusted to pH 2.6 and mixed at 0° C. with 60 mg of 1-ethyl-3-(3-dimethylaminopropyl) carbodiimide (Sigma). After 10 minutes, the reaction mixture was passed at 0° C. through a PD10 Sephadex G25 column (at pH 3) to remove excess 1-ethyl-3-(3-dimethylaminopropyl)carbodiimide Recovery of polyacrylamide from this column was essentially complete, but in order to have a full separation of polyacrylamide from 1-ethyl-3-(3-dimethylaminopropyl)carbodiimide, only the first 1.5 ml of the polyacrylamide peak, containing approximately 50 percent of the polyacrylamide added was collected. This activated polyacrylamide was kept at 0 degrees and a 25 μl aliquot was immediately passed through a TSK size exclusion guard column at a flow rate of 1 ml per minute. The excluded peak containing the activated polyacrylamide carboxyl groups emerged in less than 2 minutes, and the entire run was over in 5 minutes. The polyacrylamide concentration was calculated from the peak area measured by the refractometer (see Methods). To measure the extent of activation, another 25 μl of the activated polyacrylamide was added to 5 μl of 1 M tyramine [i.e., 4-(2-aminoethyl)phenol] at pH 8.5, (approximately a 1000 fold molar excess relative to PA carboxyl groups) and run through the TSK guard column. The absorbance of the excluded peak at 280 nM was used to calculate the amount of tyramine bound to the activated polyacrylamide. A one million dalton polyacrylamide molecule with 11 percent carboxylation has about 1560 carboxy residues. In three activation experiments we have performed, the number of activated carboxyl residues respectively per polyacrylamide molecule was theoretically 445, 298, and 423, as measured by tyramine binding immediately after separation from excess carbodiimide on a G25 Sephadex column. When activated polyacrylamide was allowed to stay at 0° C., the number of activated carboxyl groups declined with a half-life of about one hour. The activated polyacrylamide is not stored or frozen, but following measurement of the polyacrylamide concentration and activated carboxyl groups, aliquots are immediately added to protein solutions to form conjugates. The half-life of one hour allows ample time for these measurements and additions.

To verify that the activated polyacrylamide formed covalent bonds after separation from excess carbodiimide, it was reacted with mouse IgG at pH 8.5 and separated from unreacted IgG by size exclusion. When the excluded peak (putative conjugate) was boiled in 2% SDS and run on unidimensional SDS-polyacrylamide gel electrophoresis in a 10-15% gradient gel, all the protein remained at the origin, indicating that it was bound to very high molecular weight material. When the excluded peak was reduced with mercaptoethanol and then electrophoresed, a portion of the protein migrated into the gel at the rates expected for immunoglobulin heavy and light chains, indicating that while the protein was covalently bound to the polyacrylamide, the number of bonds was not excessive in that some of the light chains and heavy chains were separable on reduction by mercaptoethanol.

2. Preparation, isolation, and storage of polyacrylamide-streptavidin (PASA)

To prepare PASA, activated polyacrylamide was prepared as described above and a 550 μl aliquot containing 1 mg of the activated polyacrylamide (1 nmole) as calculated from the peak area of the excluded peak from the TSK guard column (as mentioned above) was immediately added to 6.0 mg of streptavidin (128 nmoles) in 520 μl of 0.2M borate buffer at pH 8.5. The large excess of streptavidin was used to inhibit intermolecular crosslinking of the PA by the streptavidin. After 2 hours at 0° C., PASA was isolated from the reaction mixture by size exclusion chromatography on a train of one TSK guard column followed by two 300×7.5 mm TSK 250 size exclusion columns (Bio-Rad). PASA (i.e., the conjugate of streptavidin to polyacrylamide) was found in the excluded peak, peak (conjugate), well separated from unreacted streptavidin, which could be concentrated and reused. While PASA has not been lyophilized, but has been kept at 4 degrees in a 0.125M phosphate pH 6.85 buffer for 4 months, and remained stable as shown by a biotin binding assay (see below).

3. Characterization of polyacrylamide-streptavidin (PASA).

PASA prepared and measured as described in the methods herein, had a mean of approximately 20 streptavidin molecules attached to each molecule of polyacrylamide. As measured by binding of tritiated biotin on size exclusion columns, the streptavidin molecules that were linked to polyacrylamide could bind approximately 1.4 molecules of biotin each, compared to 3.1 molecules of biotin bound per molecule of free streptavidin.

4. Characterization of antibody conjugates.

To determine its binding capacity for biotinylated proteins, PASA was incubated with differing amounts of biotinylated antibodies (11.4.1 mouse IgG anti-Kk, and K204 rat IgG anti-non k), and separated from unbound protein by size exclusion. Each molecule of PASA could bind at least 8 molecules of biotinylated IgG per molecule of PASA. When only 6 molecules of biotinylated IgG were incubated per PASA molecule, essentially all the biotinylated protein bound, and no purification of conjugate from unbound antibody was needed. The binding of biotinylated proteins to PASA is done at room temperature, at neutral pH, and occurs essentially instantaneously. We allow the reaction to proceed for 5 minutes.

5. Binding of antibody heteroconjugates to cells.

In order to test the retention of specificity by a PASA based conjugate, a heteroconjugate was constructed by mixing equal amounts of biotinylated mouse anti-Kk (B11.4.1) and biotinylated rat anti-non k (BK204) with PASA at a molar ratio of 5/1 total antibody to PASA. The resulting heteroconjugate was tested for binding to H-2k RDM4 cells and H-2d P815 cells by flow cytometry. The results are shown in Table I below.

TABLE I

Specific binding of a polyacrylamide-streptavidin based heteroconjugate with two different biotinylated antibodies (B11.4.1 anti-H-2Kk and BK204 anti-non k) to cells of two different H-2 haplotypes (H-2d P815 and H-2K RDM4).

| Antibody or conjugate | fluorescent anti-IgG against | linear fluorescence units cell | |
|---|---|---|---|
| | | P815 (H-2d) | RDM4 (h-2k) |
| PASA | mouse | 7 | 4 |
| PASA | rat | 6 | 3 |
| B11.4.1 mouse anti-Kk | mouse | 7 | 84 |
| B11.4.1 mouse anti-Kk | rat | 9 | 4 |
| BK204 rat anti-non k | mouse | 5 | 5 |
| BK204 rat anti-non k | rat | 75 | 3 |
| B11.4.1-PASA-BK204 anti-Kk, non k | mouse | 40 | 133 |
| B11.4.1-PASA-BK204 anti-Kk, non k | rat | 107 | 69 |

As seen in Table I, the biotinylated 11.4.1 anti Kk antibody by itself does not bind to the H-2d P815 cells, but can be detected on them as part of the heteroconjugate. In reciprocal fashion, the biotinylated K204 anti non k does not bind to the H-2k RDM4 cells but can be detected on them as part of the heteroconjugate. Thus, the heteroconjugate reacts with both P815 and RDM4 cells, and is detected with either fluorescent anti-mouse or anti-rat IgG, in contrast to PASA by itself with reacts with neither, or to the biotinylated antibodies which react with only one cell type and are detected with only one of the fluorescent antibodies.

6. Heteroligation of cells by the heteroconjugate.

In order to see if the heteroconjugate "B11.4.1-PASA-BK204" could heteroligate H-2d cells to H-2k cells, P815 cells and RDM4 cells were labeled with vital dyes as described in Methods. One hundred thousand cells of each type were mixed together with 0.8 μg of the heteroconjugate in a total volume of 15 μl. This mixture was kept at room temperature for 5 minutes and then centrifuged at 600 ×G for 5 minutes at 4 degrees.

Figure 2B:
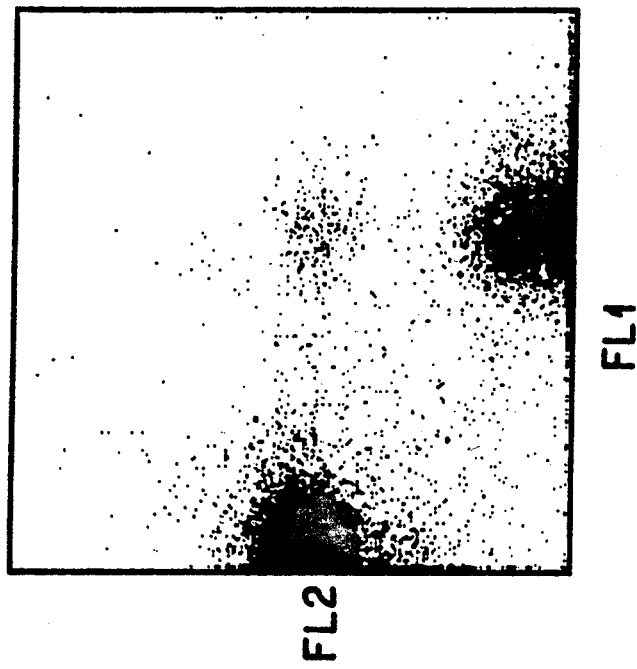
FIG. 2. "Dot plots" showing heteroligation of RDM4 cells to P815 cells by the anti H-2 k,d heteroconjugate BK204-PASA-B11.4.1. FL1 (X axis): green (CFDA) fluorescence of H-2d P815 cells. FL2 (Y axis): red (HDE) fluorescence of H-2k RDM4 cells. Heteroligated cells appear toward the upper right of each panel. The mixed cells were incubated with PASA (A), anti-non k BK204-PASA (B), anti-Kk B11.4.1-PASA (C), and anti k,d BK204-PASA-B11.4.1 (D). For each mixture 25000 events were recorded, and the percent of cells heteroligated was 2.0, 2.7, 3.0, and 40.1, respectively.
Figure 2A:
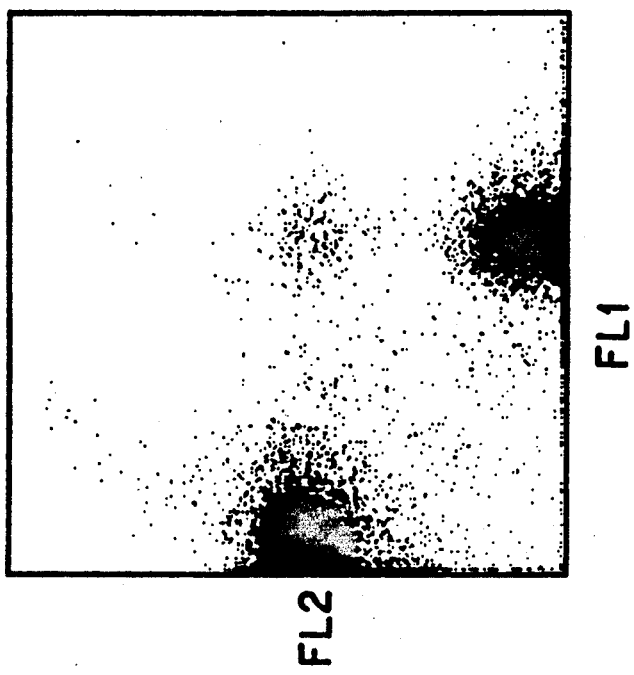
Figure 2D:
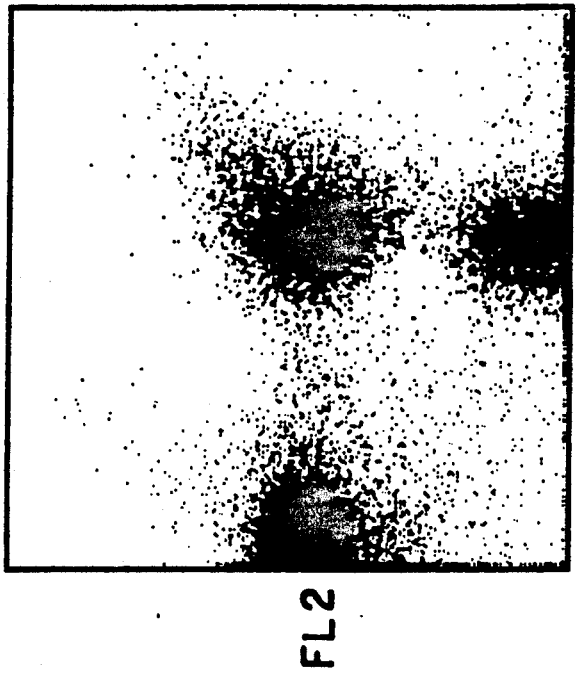
Figure 2C:
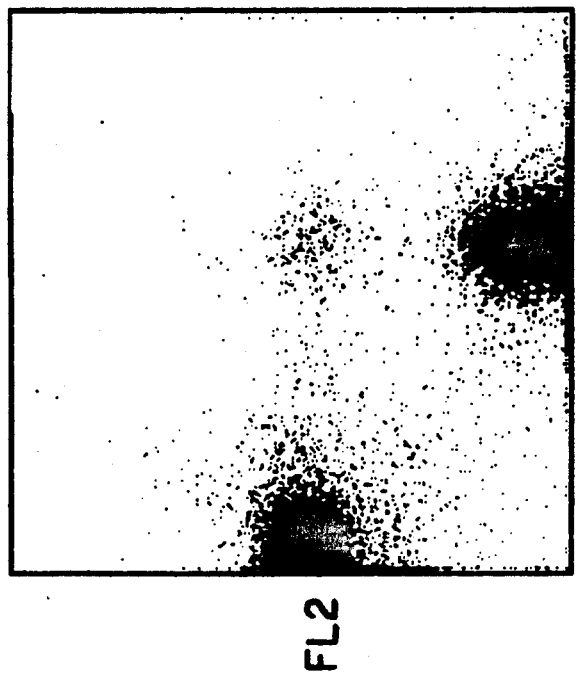

After an additional 30 minutes at 4 degrees, the pellets were resuspended in 200 μl of fluorescence buffer by gentle vortexing, and the cells examined for heteroligation by flow cytometry. As controls, the cells were treated in the same fashion with either PASA alone (FIG. 2A), or with the homoconjugates BK204-PASA (FIG. 2B) and B11.4.1-PASA (FIG. 2C). As seen in FIG. 2D, the heteroconjugate clearly heteroligated the P815 cells and the RDM4 cells to each other.

7. Labeling of cells with MHC alloantigen.

In order to label tumor cells with MHC alloantigen, PASA was incubated with a mixture of biotinylated anti-H-2Kk, and either biotinylated H-2Dd or biotinylated H-2b antigen. The conjugates were then mixed with RDM4 tumor cells. The results are shown in Table II.

TABLE II

Coating of H-2k RDM4 tumor cells with polyacrylamide-streptavidin based conjugates containing biotinylated anti-H-2Kk (B11.4.1), and either biotinylated H-2Dd or biotinylated H-2b class I MHC molecules, detected by rat anti-non k (K204), plus FITC labeled anti-rat immunoglobulin, and compared with H-2d P815 cells (Exp. 1) or with H-2b EL4 cells (Exp. 2), naturally coated with the same molecules.

| Antigen-containing heteroconjugate | Cell | linear fluorescence units |
|---|---|---|
| Exp. 1 | | |
| B11.4.1-PASA-BH-2Dd | RDM4 (H-2k) | 3 |
| | RDM4 | 33 |
| | P815 (H-2d) | 7 |
| Ex. 2 | | |
| B11.4.1-PASA-BH-2Db | RDM4 (H-2k) | 2 |
| | RDM4 | 20 |
| | EL4 (H-2b) | 19 |

As seen in Table II, when the H-2k RDM4 cells were mixed with B11.4.1-PASA-BDd conjugate, they reacted with the K204 anti-non k, showing attachment of the H-2Dd antigen to the H-2k cells. When the heteroconjugate was made with H-2b, (B11.4.1-PASA-BH-2b), the H-2k RDM4 cells again reacted with anti-non k, showing that the H-2b antigen was now attached to them. To give an approximate indication of the amount of antigen attached to them, the H-2Dd-coated RDM4 cells were compared with H-2d P815 cells. The reaction of anti-non k (K204) with other class I molecules on the P815 cells (Kd,Ld) may be the reason why P815 shows over twice the fluorescence of the H-2Dd-coated RDM4 cells. When the H-2b-coated RDM4 cells were compared with the H-2b EL4 cells, the fluorescence was the same, because the K204 antibody used to detect the antigen was also used as the immunoabsorbent to purify the H-2b antigen used in the conjugate.

These results show that polyacrylamide-streptavidin (PASA) can be used with biotinylated antibodies and antigens to construct soluble multivalent macromolecular conjugates that can specifically coat tumor cells with MHC antigens of a different haplotype. Furthermore, these results are illustrative of the general utility of either avidin or streptavidin modified water-soluble polymers such as polyacrylamide, as provided herein, in the construction of multivalent protein-protein conjugates.

REFERENCES

Abramenko T. V., Vinogradov, I. V., Kabanov V. A., Mustafaev M. I., Petrov R. V., Khaitov R. M., Filatova E. D. (1983). Immunogenicity of a conjugate of bovine serum albumin with polyacrylic acid. Zh. Mikrobiol. Epidemiol. Immunobiol. 11:86

Bayer E. A. and Wilchek M. (1980). The use of the avidin-biotin complex as a tool in molecular biology. Meth. Biochem. Analysis 26:1.

Henriksen, O., Robinson E. A., and Appella E., (1979) Purification and chemical characterization of papain-solubilized histocompatibility antigens from mouse liver. J. Biol. Chem. 254:7651.

Inman J. K. (1974) Covalent Linkage of Functional Groups, Ligands, and Proteins to Polyacrylamide Beads. Methods in Enzymology 34:30.

Inman, J. K., (1975) Thymus-independent antigens: The preparation of covalent, hapten-ficoll conjugates. J. Immunol. 114:704.

Kochetkov N. K., Dimitriev B. A., Chernyak A. Ya., Pokrovskii V. I., and Tendetnik Yu. Ya. (1982). New Type of Carbohydrate-containing artificial antigen. Synthesis and immunochemical characteristics of a carbohydrate-containing copolymer with 0:3 factor specificity of serogroup E salmonella. Doklady Akademii Nauk SSSR 263:1277.

Luce, G. G., Sharrow, S. O., Shaw, S., and Gallop, P. M. (1985) Enumeration of cytotoxic cell-target conjugates by flow cytometry using internal fluorescent stains. Biotechniques 3:270.

McKluskey J., Boyd L. F., Highet P. F., Inman J., and Margulies D. H. (1988). T cell activation by purified, soluble, class I MHC molecules: requirement for polyvalency. J. Immunol. 141:1451 Mescher M. F., Stallcup K. C., Sullivan C. P., Turkewitz A. P., and Herrman S. H. (1983) Purification of murine MHC antigens by monoclonal antibody affinity chromatography. Methods Enzymol 92:86.

Oi V. T., Jones P. P., Goding J. W., Herzenberg L. A., and Herzenberg L. A. (1978) Properties of Monoclonal Antibodies to mouse IgG Allotypes, H-2, and Ia Antigens. Current Topics in Microbiol. and Immunol. 81:115.

O'Shannessy D. J., and Quarles R. H. (1987) Labeling of the oligosaccharide moieties of immunoglobulins. J. Immunol. Methods. 99:153.

Pahler A., Hendrickson W. A., Kolks M. A., Argarana C. E., Cantor C. R. (1987) Characterization and crystallization of core streptavidin. J. Biol. Chem. 262:13933.

Petrov R. V., Khaitov, R. M., Norimov, A. Sh., Kabanov, V. A., Mustafeev, M. I., and Filatova, E. D. (1979) Immunogenicity of a complex obtained by covalent binding of bovine serum albumin with a copolymer of 4-vinylpyridine and 4-vinyl-N-acetylpyridinium bromide. Doklady Akademmii Nauk SSSR 249:249.

Printseva O. Yu., Faerman A. I., Maksimenko A. V., Tonevitsky A. G., Ilynsky O. B., Torchilin V. P. (1985) Selective killing of smooth muscle cells in culture by the ricin A-chain conjugated with monoclonal antibodies to a cell surface antigen via a dextran bridge. Experientia 41:1342.

Rihova B., Kopecek J., Kopeckova-Rejmanova P., Strohalm J., and Plocova D. (1986) Bioaffinity therapy with antibodies and drugs bound to soluble synthetic polymers. J. Chromatog. 376:221. # Siciliano R. F., Keegan A. D., Dintizis R. Z., Dintzis H. M., Shin H. S. (1985) The interaction of nominal antigen with T cell antigen receptors. I. Specific binding of multivalent nominal antigen to cytolytic T cell clones. J. Immunol. 135:906.

Smith P. K., Krohn R. I., Hermanson G. T., Mallia A. K., Gartner F. H., Provenzano M. D., Fujimoto E. K., Goeke N. M., Olson B. J., and Klenk D. C. (1985) Measurement of Protein using bicinchoninic acid. Anal. Biochem. 150:76.

Vinogradov I.V., Kabanov V. A., Mustafaev M. I., Norimov A. Sh., Petrov R. V., and Khaitov T. M. (1982). Complexes of proteins with nonnatural polycations: Thymus-independent antigens. Doklady Akademii Nauk SSSR 263:228.

The present disclosure is to be only limited by the scope of the appended claims.

What is claimed is:

1. A water-soluble avid or streptavidin modified polyacrylamide, prepared by the process steps of:
   (I) converting about 1 to 50% of the amide groups of a water-soluble polyacrylamide into carboxyl groups, said polyacrylamide being soluble in two parts of purified water, USP, at about 23° C. on a weight/weight basis;
   (II) activating, in an aqueous solution subsequent to step (I), certain carboxyl groups on said polyacrylamide with an excess of a carbodiimide;
   (III) separating the resultant product of step (II) from said excess of said carbodiimide;
   (IV) reacting, subsequent to step (III), said resultant product with an excess of avidin or streptavidin, and thereby forming said avidin or streptavidin modified polyacrylamide in situ; and
   (V) separating, subsequent to step (IV), said avidin or streptavidin modified from excess streptavidin or avidin.

2. The avidin or streptavidin modified polyacrylamide of claim 1, wherein:
   step (I) is performed at a pH of about 9-11;
   step (II) is performed at a temperature of about 0° C. and a pH of about 2-3; and
   step (IV) is performed at a temperature of about 0° C. and a pH of about 8-9.

3. The modified polyacrylamide of claim 2, wherein said modified polyacrylamide is a streptavidin modified polyacrylamide.

4. The avidin or streptavidin modified polyacrylamide of claim 1, additionally substituted, subsequent to step (V), by a variety of biotinylated antibodies, or biotinylated toxins, or biotinylated isotope-labelled proteins.

5. The avidin or streptavidin modified polyacrylamide of claim 2, additionally substituted, subsequent to step (V), by a variety of biotinylated antibodies, or biotinylated toxins, or biotinylated isotope-labelled proteins.

6. The avidin or streptavidin modified polyacrylamide of claim 3, additionally substituted, subsequent to step (V), by a variety of biotinylated antibodies, or biotinylated toxins, or biotinylated isotope-labelled proteins.

* * * * *